United States Patent [19]

Mayr et al.

[11] 4,191,745

[45] Mar. 4, 1980

[54] PREPARATION FOR THE TREATMENT OF HERPES ZOSTER AND OTHER HERPES INFECTIONS, AS WELL AS METHOD FOR MANUFACTURE THEREOF

[75] Inventors: Auton Mayr, Munich; Helmut Stickl, Krailling; Melchior Westhues, Munich, all of Fed. Rep. of Germany

[21] Appl. No.: 891,206

[22] Filed: Mar. 29, 1978

[30] Foreign Application Priority Data

Apr. 1, 1977 [DE] Fed. Rep. of Germany ....... 2714665

[51] Int. Cl.$^2$ ........................ A61K 41/00; C12K 7/00
[52] U.S. Cl. ...................................... 424/90; 424/89; 435/173; 435/236
[58] Field of Search ...................... 195/1.2; 424/89, 90

[56] References Cited

U.S. PATENT DOCUMENTS 4,053,582  10/1977  Stickl ................................. 195/1.3

*Primary Examiner*—Sam Rosen
*Attorney, Agent, or Firm*—DeLio and Montgomery

[57] ABSTRACT

The invention provides a novel preparation for treatment of Herpes zoster and other Herpes infections, comprising active principle pox and/or parapox virus of the family: poxviridae, the nucleic acids of which have been selectively damaged and a suitable carrier of said virus. A method for manufacture of the novel preparation of the invention and for treatment of Herpes zoster therewith is also provided.

7 Claims, No Drawings

PREPARATION FOR THE TREATMENT OF HERPES ZOSTER AND OTHER HERPES INFECTIONS, AS WELL AS METHOD FOR MANUFACTURE THEREOF

In recent years, the so-called factor diseases have been on the increase. These are bacterial, virus and fungus dependent, infectious diseases of mammals induced by so-called "opportunistic germs". These pathogens occur in the organism in a latent form or they exist in symbiosis with our body without causing it harm. If, however, the general resistance should be lowered by whatever factor (e.g. high-energy radiation, antimetabolites, systemic diseases of the immune apparatus, hormones, etc.), then these infectious diseases appear and may lead to symptoms which are difficult to treat. An example for this is Herpes zoster (shingles), which is induced by the varicella-zoster virus.

Herpes zoster results, after an attack of chicken pox, from a second exposure of the organism to the varicella-zoster virus and manifests itself as a predominantly neurocutaneous disease. Zoster occurs only in man; this disease does not naturally occur in animals, nor does an experimental animal model exist.

A consistent therapy for zoster is not known at the present time. Numerous attempts to develop a treatment for zoster have led to unsatisfactory results, including among others, application of a localized treatment (powder and ointment), use of steroids, and use of analgetic and antirheumatic active principles, as well as of interferonization.

Passive interferonization, that is, the application of isolated exogenic interferon, resulted only in temporary success and failed to affect the zoster decisively. More favourable results were achieved by the so-called induction of interferons, that is, by the administration of substances which induce the body cells to yield interferons. However, even these proved to be of limited effectiveness, since—to the extent that the so-called viral interferon inducers were involved—they limited their effectiveness by way of the immunization itself. Synthetic interferon inducers proved to be harmful, since they affected the genetic substance of cells. Thus to date, a satisfactory active interferonization, for which both effectiveness and harmlessness are guaranteed, has not been produced.

It is already known from DT-OS 2 437 166 that for the treatment of Herpes zoster and other viral diseases, a fowl pox virus, which has been attenuated by 420 to 800 passages through a cell culture, can be employed. Over this range of passages, the attenuated fowl pox virus has identical and stable properties.

The virus which was attenuated by 429 cell culture passages, and subsequently purified by triple clonization, has been deposited under the designation "Mayr-Stickl-Avipox-Interferon-Inducer" with the State Inoculation Institute of Northrhine Westphalia, Department for Virus Growth and Testing, Dusseldorf 4.

The disadvantage of the fowl pox virus described in DT-OS 2 437 166 resides in its retained ability to multiply.

It has now been established that pox and parapox viruses (family: poxviridae), in particular the fowl pox virus and the Orf virus, both in virulent and attenuated form, not only lose their ability to reproduce on $\gamma$-irradiation, but at the same time increase their biological effectiveness against Herpes infections; this is surprising, since in general, an inactivation treatment entails a loss in effectiveness.

The $\gamma$-irradiation that has been found suitable for such an inactivation treatment is one, which selectively damages the nucleic acids of the virus, while leaving unchanged and intact the other structures of the virus, in particular, the surface structure, the protein of the virus and the substances of the outer sheath.

Furthermore, it was unexpectedly discovered, that with the aid of virus preparations, which were treated in accordance with the invention, not only parenteral, but also local medicinal effectiveness occurs.

In order to obtain preparations in accordance with the invention, cell cultures are innoculated with the virus to be employed; at the peak of virus multiplication, the virus is harvested from the cell culture and purified by well-known methods. The purified virus harvest is tested for virus content/ml, and the virus material to be inactivated is brought to a titer of at least $10^{7.0}$ ID$_{50}$/ml (ID=Infective Dose), and preferably, the virus suspension should exceed $10^8$ ID$_{50}$/ml. However, the preparation already has an adequate effectiveness, if as a lower limit, a titer of at least approximately $5 \times 10^6$ ID$_{50}$/ml is achieved. For optimal effectiveness, a titer approaching $5 \times 10^8$ ID$_{50}$/ml is to be recommended.

For the subsequent $\gamma$-irradiation of the virus harvest obtained by the above method, an inactivation kinetics is established by well-known means for every virus strain. According to this kinetics, the irradiation treatment is continued until all viruses of the starting material have lost their ability to multiply. For the inactivation kinetics, the following factors are of importance: Type, concentration, medium and volume of the virus material, the properties of the of the container and of the energy (radiation) source. It is advisable to add suitable stabilizers to the inactivated virus materials, as for example 2% skimmed milk or peptone. Subsequently, the inactivated materials are freeze-dried, and the dried product serves as starting material for obtaining the respective final product forms of the preparation described in this patent.

The manufacture of a preparation in accordance with the invention will be described below by way of example.

The starting material was the "Mayr-Stickl-Avipox-Interferon-Inducer", which has been deposited under this designation with the Institution mentioned above. This fowl pox virus is non-pathogenic for man and animals, and is capable of multiplication in cultures of fibroblast cells obtained from fowl embryos (FHE). The virus is derived from the fowl pox strain HP-1, which was attenuated by multiple passages in FHE until the loss of virulence was achieved, and which was then plaque-purified after the 429th passage. The virus harvest of the 3rd plaque passage (i.e. the 432nd passage) is multiplied and lyophilized in FHE from leukose-free eggs. This constitutes the starting material for the seed virus of the preparation of this claim. In order to obtain the preparation of this claim, the seed virus is cultured—stationary FHE (medium: sterile bovine amnionic liquid=RAF). The virus harvests are subjected to an ultrasonic treatment, purified by fractionated centrifuging and, after adding 2.5% lactalbumin, lyophilized. The end product has a titer between $10^7$ and $5 \times 10^{8.5}$ CID$_{50}$/ml. The analysis of virus content is now carried out by well-known methods on FHE.

The virus derived from the starting material by the method described above (the virus harvest) is now inactivated with regard to its ability to multiply by γ-irradiation at a level of $10^6$ rad (cobalt bomb; output approximately 20 krad/Min. 500 ml glass container). Evidence for the inactivation comes from the insertion of a sufficient sample volume of the treated material into cultures of fibroblast cells obtained from fowl embryos. If within, at most, nine (9) days no cytopathogenic effects (CPE) caused by viruses developed on the cell mat, then this was taken as evidence for a complete inactivation.

The preparations obtained in this manner can be used in different product forms, as for example:

1. Re-suspended in sterile bi-distilled water (1 ml$=10^{7.75}$ $CID_{50}$/ml).
2. In tablet or capsule form (1 tablet or capsule$=10^{7.0}$ $CID_{50}$/ml; the tablet form is derived from the liquid phase before lyophilization).
3. As a spray (1 ml bi-distilled water and 10% glycerin$=10^{7.5}$ $CID_{50}$/ml).

The preparation in accordance with this invention may contain the usual therapeutic additives. With the aid of the preparation in accordance with this invention, an effective treatment of Herpes infections of the mammal organism, especially of Herpes zoster, can be achieved.

With regard to non-specific resistance, phagocytosis is increased after the administration of preparations in accordance with this invention, and the humoral resistance factors, especially of complement and IgM antibodies, are stimulated. In addition, the formation of interferon is induced, or an already operating production of interferon is increased, that is, existing interferon is now released. In parallel occurs an infiltration of macrophages into the spleen, liver and lymph nodes, as well as an increase of menocytes in the circulatory system. In general, the macrophage activity (phagocytosis, antigenmediation) increases up to 400 of its initial value.

The effectiveness of the preparation described in this invention may be demonstrated with the SVS-model (standardized infection of baby mice with the virus of vesicular stomatitis), which for technical reasons and because of its good reproductivity, affords a suitable test of the preparation described in this invention.

Two hundred seventy-six mice were infected with the vesicular stomatitis virus, of which 224 (81%) died within the next few days.

A group of 201 animals was subjected to a prior administration of the untreated preparation, which consisted of Avipox-virus capable of multiplication. In this case, only 85 animals, that is 42.3% when compared to the mortality of the control group, died.

A group of 125 animals was subjected to a prior administration of the preparation described in this invention. In this case, only 18 animals died. This corresponds to a mortality of 14.4%; thus, less than 1/5 of the mortality of the infected and untreated control animals was observed.

With regard to the rapidity of the occurrence of death, it was observed that the infected and untreated control animals died, on the average, after 5.3 days; those subjected to a prior administration of the untreated preparation died after 19.5 days; and those pretreated with the preparation described in this invention died after 33.3 days.

The following table similarly demonstrates that the effectiveness index increases from 48 to 83 for an equal virus antigen quantity per dose.

TABLE

| | TEST OF EFFECTIVENESS OF THE PREPARATION IN ACCORDANCE WITH THE INVENTION FOR THE VSV-MODEL | | | | |
|---|---|---|---|---|---|
| Experimental Group | Number of Trials | Mortality | Index of Effectiveness | Significance | Average Day of Death |
| Untreated preparation according to DT-OS 2 437 166 | 8 | 85/201 42.3% | 48 | +++ | 19.5 |
| Preparation in accordance with this invention | 5 | 18/125 14.4% | 82 | ++++ | 33.3 |
| Placebo (RAF) | 11 | 224/276 81.2% | — | ---- | 5.3 |

Comments: Calculation of significance performed with the Chi-Square Test, for 0.01

A further difference between the untreated preparation (reference preparation) and the preparation in accordance with this invention becomes apparent in the phagocytosis investigation. If mice are given an intraperitoneal injection of the untreated preparation (which is capable of multiplication), then an increased phagocytosis results, as measured by carbon particle clearance. The administered preparation, diluted as much as 1:16, is still able to effect an increase in phagocytosis after 48 hours. For the preparation in accordance with the invention, the same effect at the same point in time can still be achieved for a dilution of 1:64.

Examples of the application of the preparation described in this invention:

EXAMPLE 1

An 11 year old girl with a facial zoster which had been in evidence for three days. Doses of 0.5 ml of the preparation, which was produced as described above, are introduced intranasally with a sprayer and inhaled. Three administrations on the first day, two on the second, and one on the third.

Already after 48 hours, the pain decreases and crusting of the facial zoster begins. (pictures are available.) The crust is shed after 12 days (this does not usually occur before 32 days!).

EXAMPLE 2

A 51 year old man in generally poor condition and duodenal ulcer. Zoster at the level of the 7. to the 10. rib, extending from the nipple to the back. Numerous vesicles, eruption of the vesicles until the 4th day after the first manifestation of the vesicles. Severe pain with pain attacks, especially at night.

Administration of a total of 48 chewable tablets, as described above, with 6 chewable tablets at a time, at intervals of 4 to 6 hours (while maintaining a night break of at least 8 hours). Treatment for 3 days. Mitigation of pain on the day initial treatment, disappearance of pain on the third day of treatment. Crusting begins on the 6th day of treatment, shedding of the crust on the 18th day. With the successful treatment of the severe zoster, an improvement of the duodenal ulcer occurs. Attendant catarrhal manifestations of the sinuses also diminished, facilitating nose breathing.

EXAMPLE 3

A 23 year old girl with chronically recurring cystitis (Coli-bacteria, fungus in urine culture). Repeated attempts using conventional therapy did not bring about permanent cure. Administration of 36 tablets, as prepared above, within 3 days. Amelioration of the symptoms (polyuria and pain on urinating) after one week and subsequently, their complete absence for a longer time.

What is claimed is:

1. A preparation for the treatment of Herpes zoster and other Herpes infections comprising an effective amount of an active principle obtained from pox and/or parapox virus of the family: poxyviridae which has suffered selective damage to its nucleic acids by $\gamma$-irradiation, without change or damage to the other structures of the virus including but not limited to its surface structure, the virus protein and the substance of the outer sheath, and a suitable carrier for said active principle.

2. The preparation in accordance with claim 1, wherein said virus is the Avipox-virus, which has been deposited under the designation "Mayr-Stickl-Avipox-Interferon-Inducer", and which has been attenuated by 420 to 800 passages through a cell culture and has retained its identity and stability over said range of passages.

3. The preparation in accordance with one of the claims 1 or 2, wherein said virus was inactivated by $\gamma$-irradiation at a level of between $8 \times 10^5$ to $10^7$ rad.

4. The preparation in accordance with one of the claims 1 or 2, wherein said virus has a titer of approximately $5 \times 10^{6.0}$ ID$_{50}$/ml.

5. The preparation in accordance with one of the claims 1 or 2, wherein said preparation contains additional suitable stabilizers.

6. A method for production of the preparation in accordance with one of the claims 1 or 2, comprising (1) innoculating cell cultures with an active principle of pox or parapox viruses of the family: poxviridae, at the peak of virus multiplication, (2) harvesting and purifying said virus, (3) preparing a titer of approximately $5 \times 10^6$ to $5 \times 10^8$ ID$_{50}$/ml of the virus suspension, (4) subjecting said titer to $\gamma$-irradiation whereby the nucleic acids of said virus are selectively damaged without change or damage to the other structures of the virus, including but not limited to its surface structure, the virus protein and the substance of the outer sheath and, (5) optionally adding stabilizers and/or other therapeutic additives, whereby a preparation which can be administered either intraperitoneally or locally is prepared.

7. The method in accordance with claim 6, wherein said Avipox-virus, which has been deposited under the designation "Mayr-Stickle-Avipox-Interferon-Inducer", is attenuated by 420 to 800 passages through a cell culture while retaining its identity and stability over this range of passages, prior to being subjected to $\gamma$-irradiation.

* * * * *